United States Patent [19]

Allphin et al.

[11] Patent Number: 5,319,088

[45] Date of Patent: Jun. 7, 1994

[54] SELECTIVE GAS PHASE CHLORINATION OF POLYCHLORINATED β-PICOLINES TO PRODUCE 2,3,5,6-TETRACHLOROPYRIDINE AND ITS PRECURSORS

[75] Inventors: Clark P. Allphin, Concord; Michael A. DesJardin, San Ramon, both of Calif.; Arnold D. Harley, Baton Rouge, La.

[73] Assignee: DowElanco, Indianapolis, Ind.

[21] Appl. No.: 798,683

[22] Filed: Nov. 26, 1991

[51] Int. Cl.$^5$ .................. C07D 213/61; C07D 213/26
[52] U.S. Cl. .................................. 546/345; 546/346
[58] Field of Search .......................... 546/345, 346

[56] References Cited

U.S. PATENT DOCUMENTS

| | | | |
|---|---|---|---|
| 3,186,994 | 6/1965 | Johnson et al. | 546/345 |
| 3,370,062 | 2/1968 | Corran | 546/345 |
| 3,420,883 | 1/1969 | Taplin, III | 544/107 |
| 4,205,175 | 5/1980 | Bowden et al. | 546/345 |
| 4,241,213 | 12/1980 | Nishiyama et al. | 546/345 |
| 4,281,135 | 7/1981 | Perettie et al. | 546/345 |
| 4,429,132 | 1/1984 | Whittaker | 546/346 |
| 4,490,534 | 12/1984 | Fujikawa et al. | 546/345 |
| 4,752,644 | 6/1988 | Sharvit et al. | 546/345 |
| 4,785,112 | 11/1988 | DesJardin et al. | 546/345 |
| 4,801,716 | 1/1989 | Sharvit et al. | 546/345 |
| 4,810,797 | 3/1989 | Sharvit et al. | 546/345 |
| 4,968,807 | 11/1992 | Humphreys et al. | 546/345 |

OTHER PUBLICATIONS

I. Sangyo, Japanese Kokai JP 58,206,564 *Chem. Abst.*, vol. 100, 138966j (1984).

*Primary Examiner*—Alan L. Rotman
*Attorney, Agent, or Firm*—D. Wendell Osborne

[57] ABSTRACT

2,3,5,6-Tetrachloropyridine, and 2,3-dichloro-5-(trichloromethyl)pyridine are prepared by selectively chlorinating polychlorinated β-picolines in the vapor phase between about 250° and 450° C. in the presence of specific Lewis acid halide catalysts on an inorganic support. The gamma position on the pyridine ring is usually not chlorinated in the starting material or reaction products. These compounds are useful intermediates to produce insecticides and herbicides.

20 Claims, No Drawings

SELECTIVE GAS PHASE CHLORINATION OF POLYCHLORINATED β-PICOLINES TO PRODUCE 2,3,5,6-TETRACHLOROPYRIDINE AND ITS PRECURSORS

BACKGROUND OF THE INVENTION

1. Field of the Invention

The present invention relates to the selective vapor phase chlorination of polychlorinated β-alkylpyridines to produce useful higher chlorinated compounds and/or intermediates. More specifically, the invention relates to the selective gas phase chlorination of chlorinated β-picolines to produce 2,3,5,6-tetrachloropyridine, and other useful chemical intermediates, e.g. to produce commercial insecticides or herbicides.

2. Description of Related Art 2,3,5,6-Tetrachloropyridine and 2,3-dichloro-5-(trichloromethyl)pyridine are chemical intermediates which are very useful in the production of commercial insecticides and herbicides.

A number of processes are known to produce 2,3,5,6-tetrachloropyridine (Sym-Tet), usually by liquid phase chlorination. When vapor phase chlorination without catalyst is used, the yields and selectivity of chlorination are poor and the reactions are relatively slow. Further, because of the lack of selectivity, a significant amount of by-products and waste products are formed.

Some references of interest include:

H. Johnson et al. in U.S. Pat. No. 3,186,994 disclose the vapor phase chlorination of alpha-picoline to produce alpha-trichloromethyl pyridines.

J. A. Corran in U.S. Pat. No. 3,370,062 discloses a gas phase chlorination to produce pentachloropyridine. Suitable staring materials include pyridine and methylpyridines. Porous materials such as silica, alumina or combinations thereof can be used. 2-Methylpyridine is chlorinated in the presence of silica to produce pentachloropyridine.

W. H. Taplin III in U.S. Pat. No. 3,420,833 discloses the vapor phase chlorination of pyridine and isomeric picolines (e.g. alpha and gamma).

R. Nishiyama et al. disclose in U.S. Pat. No. 4,241,213 that 2-chloro-5-trichloromethyl pyridine is produced by reacting beta-picoline with chlorine in a gaseous phase at 300°–500° C. The reaction can be carried out in the presence of a porous material, e.g., silica, alumina, silicon carbide.

R. D. Bowden et al. in U.S. Pat. No. 4,205,175 disclose the vapor phase preparation of partially-chlorinated derivatives of 3-methylpyridine having a single chlorine atom substituted for hydrogen on the pyridine ring and 2 or 3 chlorine atom substituents on the methyl group.

J. Perettie et al. in U.S. Pat. No. 4,281,135 disclose the liquid phase chlorination at about 220° C. at about 50 psig of 2,6-dichloropyridine in the presence of alumina, iron or silica to produce 45% of 2,3,5,6-tetrachloropyridine.

G. Whittaker in U.S. Pat. No. 4,429,132 discloses the reaction of chlorine in the vapor phase with 3-methylpyridine at 225°–325° C. to produce 3-(trichloromethyl)pyridines in the presence of a metal oxide or metal halide catalyst. The catalyst may be a chloride or an oxide of copper, silica, magnesium, calcium, zinc, etc. Inorganic and organic gaseous diluents can be used.

K. Kujikawa et al. in U.S. Pat. No. 4,490,534 disclose a process to produce 3-chloro-5-(trifluoromethyl)pyridine. The chlorination takes place in a reaction zone in a reactor. The catalyst may be comprised of iron, antimony, copper or zinc chlorides, optionally on a carrier such as carbon, zeolite or pumice. The examples only describe trifluoromethyl reactants and trifluoromethyl containing products.

J. Sharvit et al. in U.S. Pat. No. 4,752,644 disclose the preparation of 2,3,5,6-tetrachloropyridine by direct chlorination of alpha-picoline in the gas phase with chlorine at about 200° C. in the presence of water and a catalyst.

M. A. DesJardin et al. in U.S. Pat. No. 4,785,112 disclose a process for the vapor phase chlorination of 2,6-dichloropyridine to produce 2,3,6-trichloropyridine selectively over isomeric 2,4,6-trichloropyridine. 2,3,6-Trichloropyridine, when chlorinated, produces symmetrical 2,3,5,6-tetrachloropyridine in high selectivity over isomeric unsymmetrical 2,3,4,6-tetrachloropyridine.

J. Sharvit et al. in U.S. Pat. No. 4,810,797 disclose the preparation of polychlorinated pyridines by reacting chlorine in the gas phase with partially chlorinated pyridines at about 200° C. in the presence of a catalyst, e.g. pumice and a Lewis acid halide.

I. Sangyo in Japanese Kokai JP 58,206,564 (*Chem. Abst.*, Vol. 100, 138965j (1984) discloses the vapor phase catalytic chlorination of chlorinated pyridine derivatives. 2,6-Dichloropyridine, carbon tetrachloride and chlorine are contacted with solid ferric chloride/carbon catalyst at 220° C. to produce 2,3,5,6-tetrachloropyridine (72.9%) and 2,3,6-trichloropyridine (8.8%).

All of the patents, references, articles, standards and the like cited in this application are hereby incorporated herein by reference.

None of these references individually or as a group disclose or suggest the present invention.

It is extremely useful to have a vapor phase selective chlorination of a polychlorinated β-alkylpyridine (and-/or β-picoline) using chlorine in the presence of certain Lewis acid/or halide catalysts to produce 2,3,5,6-tetrachloropyridine and/or its precursors (including chlorinated picolines). The present invention provides such a process.

SUMMARY OF THE INVENTION

The present invention relates to a process for the production of 2,3,5,6-tetrachloropyridine or the product polychlorinated picoline of the formula:

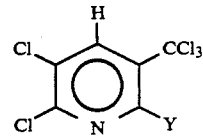

wherein Y represents H or Cl,
by the selective gas phase chlorination of a starting polychloropicoline of the formula:

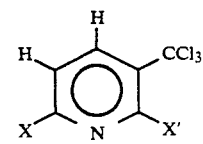

wherein X and X' each independently represent H or Cl with the proviso that when Y in the product polychlorinated picoline represents H, X' cannot represent Cl, or a mixture of these polychloropicolines, which process comprises contacting the starting polychloropicoline in the gas phase with chlorine, optionally in the presence of a gaseous diluent, at a temperature of between about 250° and 450° C. and in the presence of at least one Lewis acid catalyst deposited on an inorganic support.

In another aspect, the invention relates to the process which further includes:

collecting the polychlorinated pyridine or β-picoline product at a temperature of about 100° C. or lower.

In another aspect, the above process is one wherein the starting polychlorinated pyridine is 2-chloro-5-(trichloromethyl)pyridine, the gaseous diluent is selected from nitrogen and carbon tetrachloride or a combination thereof, the temperature is between about 300° and 400° C. at greater than atmospheric pressure, and the product comprises 2,3,5,6-tetrachloropyridine, 2,3-dichloro-5-(trichloromethyl)pyridine, 2,6-dichloro-3-(trichloromethyl)pyridine, 2,3,6-trichloro-5-(trichloromethyl)pyridine or mixtures thereof.

DETAILED DESCRIPTION OF THE INVENTION AND PREFERRED EMBODIMENTS

Definitions

As used herein:

"Catalyst support" or "inorganic support" refers to those natural or artificial inorganic materials (e.g. clays) and others that are conventional in this art (see U.S. patents above). Preferably, the clays are anhydrous. Under the reaction conditions using gaseous chlorine the clays are quickly chlorinated. Preferred supports include activated carbon, gamma-alumina, montmorillonite, diatomaceous earth, pumice, silica or combinations thereof.

"Halogenated hydrocarbons" refers to fluorinated, chlorinated or brominated hydrocarbons which are gaseous at 250° to 400° C. FREON ® compounds and chlorinated hydrocarbons are preferred, especially chlorinated hydrocarbons, such as carbon tetrachloride, tetrachloroethylene or mixtures thereof.

"Lewis acid catalyst" refers to those catalysts conventional in the art as being able to accept electrons. Lewis acid halides are preferred and include, for example, zinc chloride, nickel chloride, ferric chloride and the like.

"Unreactive gas" refers to helium, nitrogen or argon, preferably nitrogen.

Beta-picoline chlorinates in many separate steps to produce the various polychlorinated picolines. However, only certain pathways are available to selectively produce the desired compound 2,3,5,6-tetrachloropyridine (Sym-tet) or precursors to Sym-tet or higher polychlorinated picolines. The beta-trichloromethylpicoline undergoes chlorinolysis under the chlorination reaction conditions to produce desired Sym-Tet having hydrogen substitution of the carbon atom at position four.

2,3,5,6-Tetrachloropyridine, its precursors and higher chlorinated picolines are produced in good yield and with excellent selectivity in the process of the present invention by chlorination of β-picolines.

Chlorine and the polychloro-β-picoline reactant are combined and allowed to react in the vapor phase. Any reactor which is suitable for vapor phase chlorination reactions can be used in the process. Such reactors may be designed for either batch or continuous operations. However, those designed for continuous operation are preferred. Additionally, the reactor may be designed for plug flow, turbulent flow, transition flow or other types of flow and may involve plain, baffled or packed cavities. Generally, such reactors of this art are constructed so that there is efficient mixing of chlorine and the compound to be chlorinated. This is variously accomplished by means of inlet patterns, turbulent flow, reactor packing, and the like. One type of reactor suitable for the process and its operation is described in U.S. Pat. No. 4,429,132. Similar reactors of the art can be modified to alter performance, such as by the addition in the vicinity of the reactor outlet of secondary means for injecting diluents into the reactor. This is done to improve the uniformity and control of the temperature within the reactor when the reactor is used for exothermic processes like those of the present invention.

Sufficient chlorine is employed in the process to effect the desired chlorination and to provide a suitable reaction rate, but not so much as to create a chlorine recycle problem. The molar ratio of chlorine to polychloropicoline reactant employed generally ranges from about 2:1 to about 40:1. Preferably, ratios of about 3:1 to about 30:1 and more preferably, ratios of at least 6:1 to about 30:1 are employed.

An inert diluent is normally employed in the process as an aid to mixing and to promote temperature and flow rate control. Halocarbons which are unreactive with to the organic compound in the process (but may activate the catalyst), such as carbon tetrachloride and tetrachloroethylene, and unreactive gases, such as nitrogen and argon, are typical examples. Carbon tetrachloride and nitrogen, used separately or together, are preferred. The means of introducing the inert diluent into the reactor is not critical, but it is often preferred to introduce it as a mixture with the polychloropicoline reactant.

The weight ratio of diluent to polychloro-β-picoline reactant is typically about 20:1 to about 0.5:1. The present process gives 2,3,6-trichloropyridine or 2,3,5,6-tetrachloropyridine in high selectivity and good yield when the reactor is maintained at about 250° C. to about 450° C. Above this temperature, the selectivity of the reaction to produce the desired chloropyridines decreases, and over-chlorination to pentachloropyridine takes place. As a result of high temperature, the higher yields of the by-products cause the process not to be commercially useful.

Reaction temperatures above about 320° C. are preferred and those above about 340° C. are especially preferred. Reaction temperatures below about 380° C. are preferred.

The pressure in the reactor is not critical. Pressures from atmospheric to about 200 psi are typical and from atmospheric to about 50 psi are preferred. Typically, the reactor pressure is simply that which normally develops in the reactor under the conditions employed although the reaction rate expected is faster at higher pressures and higher pressures may, therefore, be preferred.

The chlorination reaction mixture is retained in the reactor until a significant portion of the reactant, e.g. 2,6-dichloro-3-trichloromethylpyridine has been consumed. Reaction times (retention times in continuous reactors) of about 0.1 sec to about 60 sec are typical, while times of about 1.0 sec to about 30 sec ar preferred. Reaction times are generally controlled by the size and shape of the reactor and the ratios and flow rates of the reactants and diluents employed.

At the conclusion of the reaction period, the reaction mixtures obtained are usually cooled to condense the organic constituents, preferably below 100° C. and, optionally, the hydrogen chloride by-product. This is typically accomplished by passing the vapors through a quantity of cooled organic solvent, such as carbon tetrachloride or methylene chloride. Carbon tetrachloride is preferred. It is often convenient to employ a quantity of previously obtained reaction product for this purpose. Typically, the organic components of the mixture are condensed and the major portion of the hydrogen chloride by-product is allowed to exit the system as a gas. Condensation of the reaction products by external cooling is also a suitable method.

The 2,3,6-trichloro-5-(trichloromethyl)pyridine and 2,3,5,6-tetrachloropyridine and other products of the process are separable from the condensate described above by conventional means. Typically, the condensate is distilled using one or more distillation apparati. Unreacted starting materials and intermediates have a different boiling point than the desired products and can be readily separated and recovered by distillation. They can be recycled to the chlorination reactor to improve the efficiency of the process. Over-chlorination by-products can be readily separated by distillation. Isomers can be removed by careful fractional distillation, by crystal refining, by recrystallization from appropriate organic solvents, or by other conventional means.

It is contemplated within this process that the partial polychlorination of β-picoline may occur in one reactor in the liquid or gaseous phase, optionally followed by separation of the components, then followed by selective catalytic vapor phase chlorination as is described by the process herein. The final polychlorinated product is separated into its components by conventional procedures.

Referring to Examples 1-7 described below, it is apparent that the alumina (Example 2), zinc chloride on silica (Examples 3 and 4), and zinc chloride on montmorillonite (Example 7) catalysts promote a much higher 3-position selectivity for the chlorination of β-2-Tet. The montmorillonite, nickel chloride on silica, and KA-O do not affect the 3-position selectivity for chloropicoline chlorination as much.

The 5% zinc chloride o montmorillonite (Example 7) exhibits much better selectivity than either the 5% zinc chloride on silica or the montmorillonite alone. The combination appears to have much higher Lewis acidity, as determined from pulse chemisorption measurements with ammonia.

The following Examples are presented to be descriptive and illustrative only. They are not to be construed to be limiting in any way.

General Experimental Procedures

The catalyst is loaded in the middle section of a 25 mm diameter×740 mm long PYREX® tubular reactor. The catalyst is supported by PYREX® wool plugs above and below. A 150 mm bed of PYREX® beads is packed above the catalyst to facilitate vaporization of the liquid feed mixture. A 6 mm OD thermowell runs through the center of the reactor. Thermocouples at the top and bottom are for monitoring purposes. The reactor is centered axially in a cylindrical ceramic fiber heater, and the temperature between the heater and the reactor wall is measured and controlled.

The chemical reactor is heated to between about 250° and 400° C., preferably about 360° C. A small nitrogen flow (between 20 and 50 sccm) purges the catalyst during heating and for 30 min after reaching the desired temperature. The nitrogen flow is then stopped, and chlorine is fed into the system, at desired flowrates for approximately 15 min before the remaining reactants are introduced.

The catalyst mass also includes any water adsorbed onto the catalyst. The "recovered catalyst mass" is essentially water-free. The "temperature" is the control temperature of the reactor wall. The "feed purity" is the purity of the 2-chloro-5-trichloromethylpyridine. For Examples 4–6, the major impurity in the feed is 2,6-dichloro-3-(trichloromethyl)pyridine.

A solution of 10% by weight of 2-chloro-5 trichloromethylpyridine in carbon tetrachloride is pumped to the top of the reactor set-up. The liquid vaporizes on the PYREX® beads, and is mixed with the chlorine vapor, which is also fed to the top of the reactor. The product from the reactor then flows into a cold trap assembly immersed in ice (0° C.). The noncondensed vapors pass to a "scrubber trap" containing 10 wt % caustic (NaOH) to neutralize acid gases.

The product is collected from the cold trap. All associated glassware is rinsed with carbon tetrachloride, which is then added to the product mixture. The total product is sampled, and is analyzed by internal standard capillary gas chromatography. Small amounts of acid chloride are sometimes present in the product, which are quantified by derivation with methanol to form the corresponding methyl esters. The acid chlorides are not included in the following Table 3, as they are minor components.

The catalysts tested include the following:

TABLE 1

| Catalyst | Description |
| --- | --- |
| 1 | Clay carrier KA-0 from Sued-Chemie, 88 m²/g. |
| 2 | Gamma alumina, Calsicat #93R-018A, ⅛ in Pellets, 166 m²/g. |
| 3 | 6.0% Zinc chloride on silica, 2 mm spheres about 200 m²/g. |
| 4 | 6.0% Zinc chloride on silica, 2 mm spheres about 200 m²/g. |
| 5 | Montmorillonite carrier K-306, 7 × 14 mesh, 224 m²/g. |
| 6 | 5.0% Nickel chloride on silica, 2 mm spheres, about 200 m²/g. |
| 7 | 5% Zinc chloride on montmorillonite, 7 × 14 mesh, about 200 m²/g |

The Experiment numbers in Tables 2 and 3 below refer to these catalysts (or catalyst mixtures).

In Table 2, the catalysts for Examples 3, 4, 6 and 7 were prepared by standard wet impregnation methods, starting with aqueous solutions of either nickel chloride or zinc chloride.

TABLE 2

EXAMPLE 1-7: REACTION CONDITIONS

| Example # | 1 (Clay) | 2 (Alumina) | 3 (ZnCl2/ silica) | 4 (ZnCl2/ silica) | 5 (Mont.) | 6 (NiCl2/ silica) | 7 (ZnCl2/ (Mont.) |
|---|---|---|---|---|---|---|---|
| Catalyst Mass, g | 36.2 | 54.6 | 23.2 | 23.6 | 27.3 | 25.3 | 28 |
| Rec. cat. mass, g | 35.8 | 41.2 | 23.3 | 24.1 | 26.7 | 18.8 | nd |
| Cl2 flow, sccm | 80.6 | 80.6 | 80.6 | 96.3 | 96.3 | 96.3 | 96.3 |
| 2-Tet flow, sccm | 36 | 36 | 36 | 18 | 19 | 21 | 8.7 |
| CCl4 flow, sccm | 251 | 251 | 240 | 134 | 134 | 146 | 110 |
| Temperature, °C. | 360 | 360 | 350 | 385 | 385 | 385 | 385 |
| feed purity, % | 100 | 100 | 100 | 97 | 97 | 97 | 100 |
| Run duration, min | 133 | 34 | 103 | 275 | 278 | 223 | 150 | nd = not determined

TABLE 3

EXPERIMENTAL RESULTS FOR EXAMPLES 1-7
(Mass % by Capillary Gas Chromatography)

| Example # | 1 (Clay) | 2 (Alumina) | 3 (ZnCl2/ silica) | 4 (ZnCl2/ silica) | 5 (Mont.) | 6 (NiCl2/ silica) | 7 (ZnCl2/ (Mont.) |
|---|---|---|---|---|---|---|---|
| 236-Tri | 0.4 | 0.0 | 0.5 | 3.9 | 14.0 | 4.2 | 4.9 |
| UTCP | 0.0 | 0.0 | 0.0 | 0.7 | 1.9 | 0.9 | 0.4 |
| STCP | 0.1 | 27.7 | 0.2 | 4.3 | 5.9 | 2.1 | 10.6 |
| β2-TET | 86.6 | 1.7 | 79.2 | 44.0 | 30.8 | 58.7 | 27.9 |
| PCP | 0.0 | 14.1 | 0.0 | 0.6 | 0.6 | 0.3 | 0.5 |
| β23-PENTA | 1.0 | 23.7* | 7.5 | 13.4 | 4.9 | 2.6 | 21.0 |
| β26-PENTA | 8.8 | 0.2* | 8.0 | 19.0 | 31.5 | 24.2 | 12.8 |
| β236-HEX | 0.1 | 21.8* | 1.1 | 7.8 | 5.4 | 1.0 | 13.8 |
| Recovery, % | 88 | 46 | 143 | 111 | 101 | 102 | 77 |

*Present as the acid chloride derivative
236-Tri = 2,3,6-Trichloropyridine
UTCP = 2,3,4,6-tetrachloropyrdine
STCP = 2,3,5,6-tetrachloropyridine Sym-tet - Desired Product
β2Tet = 2-chloro-5-trichloromethylpyridine
PCP = pentachloropyridine
β23-PENTA = 2,3-dichloro-5-(trichloromethyl)pyridine - also a desired product
β26-PENTA = 2,6,-dichloro-5-(trichloromethyl)pyridine - also a desired product
β236-HEX = 2,3,6-trichloro-5-(trichloromethyl)pyridine - also a desired product While only a few embodiments of the invention have been shown and described herein, it will become apparent to those skilled in the art that various modifications and changes can be made in the process to obtain selective chlorination of polychloro-β-picolines to produce useful products without departing from the spirit and scope of the present invention. All such modifications and changes coming within the scope of the appended claims are intended to be carried out thereby.

We claim:

1. An improved process for the production of 2,3,5,6-tetrachloropyridine or a product polychlorinated picoline of the formula:

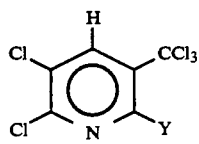

wherein Y represents H or Cl,
by the selective gas phase chlorination of a starting polychloropicoline of the formula:

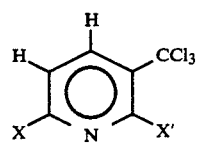

wherein X and X' are each independently selected from H or Cl, with the proviso that when Y in the product polychlorinated picoline represents H, X' cannot represent Cl, or
a mixture of said polychloropicolines, which process comprises; contacting the starting polychloropicoline in the gas phase with chlorine under gaseous-solid heterogeneous catalysis conditions, optionally in the presence of a gaseous diluent, at a temperature of between about 250° and 450° C. and in the presence of at least one solid Lewis acid catalyst of zinc chloride deposited on a solid inorganic support selected from activated carbon, gamma-alumina, montmorillonite, diatomaceous earth, pumice, silica or combinations thereof.

2. The improved process of claim 1 which further includes:
collecting the polychlorinated β-picoline product having 5 or 6 chlorine atoms, 2,3,5,6-tetrachloropyridine or a combination thereof at a temperature of about 100° C. or lower.

3. The improved process of claim 1 wherein the chlorination temperature is between about 300° and 400° C.

4. The improved process of claim 1 wherein the starting pyridine comprises 2-chloro-5-(trichloromethyl)-pyridine 2,6-dichloro-3-(trichloromethyl)pyridine, or mixtures thereof.

5. The improved process of claim 4 wherein the support is montmorillonite.

6. The improved process of claim 4 wherein the inorganic support is silica.

7. The improved process of claim 4 wherein the inorganic support is gamma-alumina.

8. The improved process of claim 1 wherein the gaseous diluent is selected from helium, nitrogen, argon or gaseous halogenated hydrocarbons.

9. An improved process for the production of 2,3,5,6-tetrachloropyridine or a product polychlorinated picoline of the formula:

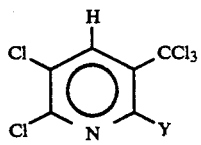

wherein Y represents H or Cl,
by the selective heterogenous gas-solid phase chlorination of a starting polychloropicoline of the formula:

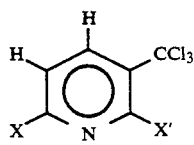

wherein X and X' are each independently selected from
H or Cl, with the proviso that when Y in the product polychlorinated picoline represents H, X' cannot represent Cl, or
a mixture of said polychloropicolines, which process comprises:
contacting the starting polychloropicoline in the gas phase with chlorine under gaseous-solid heterogeneous catalysis conditions, optionally in the presence of a gaseous diluent, at a temperature of between about 300° and 400° C. and in the presence of at least one solid Lewis acid catalyst of zinc chloride deposited on a solid inorganic support selected from activated carbon, gamma-alumina, montmorillonite, diatomaceous earth, pumice, silica or combinations thereof.

10. The improved process of claim 9 wherein the reaction time of contact is between about 0.1 to 60 sec, and the temperature is between about 340° and 380° C.

11. The improved process of claim 10 wherein the contact reaction time is between about 1.0 to 30 sec, and the temperature is about 360° C.

12. The improved process of claim 9 wherein the support is silica.

13. The improved process of claim 9 wherein the support is montmorillonite.

14. The improved process of claim 9 wherein the support is gamma-alumina.

15. The improved process of claim 9 wherein the molar ratio of chlorine to polychloropyridine reactant is between about 2:1 and 40:1.

16. The improved process of claim 9 wherein the weight ratio of diluent to reactant is between about 20:1 to 0.5:1.

17. The improved process of claim 1, wherein the sum of the weight percent of 2,3,5,6-tetrachloropyridine, 2,3-dichloro-5-(trichloromethyl)pyridine, and 2,3,6-trichloro-5-trichloromethyl)pyridine in the reaction product is greater than about 30% by weight, excluding the sum of the weight percent of the starting polychlorinated picoline and 2,6-dichloro-3-(trichloromethyl)pyridine in the reaction product.

18. The improved process of claim 4 wherein the sum of the weight percent of 2,3,5,6-tetrachloropyridine, 2,3-dichloro-5-(trichloromethyl)pyridine, and 2,3,6-trichloro-5-trichloromethyl)pyridine in the reaction product is greater than about 30% by weight, excluding the sum of the weight percent of the starting polychlorinated picoline and 2,6-dichloro-3-(trichloromethyl)pyridine in the reaction product.

19. The improved process of claim 12 wherein the sum of the weight percent of 2,3,5,6-tetrachloropyridine, 2,3-dichloro-5-(trichloromethyl)pyridine, and 2,3,6-trichloro-5-trichloromethyl)pyridine in the reaction product is greater than about 30% by weight, excluding the sum of the weight percent of the starting polychlorinated picoline an 2,6-dichloro-3-(trichloromethyl)pyridine in the reaction product.

20. The improved process of claim 14 wherein the sum of the weight percent of 2,3,5,6-tetrachloropyridine, 2,3-dichloro-5-(trichloromethyl)pyridine, and 2,3,6-trichloro-5-trichloromethyl)pyridine in the reaction product is greater than about 30% by weight, excluding the sum of the weight percent of the starting polychlorinated picoline and 2,6-dichloro-3-(trichloromethyl)pyridine in the reaction product.

* * * * *